United States Patent [19]

Stock et al.

[11] 4,348,262

[45] Sep. 7, 1982

[54] REFINING TETRAHYDROFURAN

[75] Inventors: Albert M. Stock, LaPorte; Wilson S. Tse, Houston, both of Tex.

[73] Assignee: E. I. Du Pont de Nemours and Company, Wilmington, Del.

[21] Appl. No.: 259,954

[22] Filed: May 4, 1981

Related U.S. Application Data

[63] Continuation of Ser. No. 151,242, May 19, 1980, abandoned.

[51] Int. Cl.$^3$ .............................................. B01D 3/34
[52] U.S. Cl. ...................................... 203/37; 549/429
[58] Field of Search ........... 260/346.11, 333, 346.1 R; 203/36, 37

[56] References Cited

U.S. PATENT DOCUMENTS 4,093,633  6/1978  Tanabe et al. ................. 260/346.11
4,197,248  4/1980  Copelin et al. ................ 260/346.11

FOREIGN PATENT DOCUMENTS 1313325  of 0000  United Kingdom .

OTHER PUBLICATIONS

Chemical Engineer's Handbook, Perry, 4th ed., 1963, pp. 23-5 and 23-6.

*Primary Examiner*—Frank Sever

[57] ABSTRACT

In the refining of crude acidic tetrahydrofuran prepared from acetylene and formaldehyde, corrosion of refining equipment and formation of color-producing methacrolein can be minimized by bringing the pH value of the crude tetrahydrofuran to within the range 5–11 before the refining step.

4 Claims, No Drawings

_4,348,262_

REFINING TETRAHYDROFURAN

CROSS REFERENCE TO RELATED APPLICATION

This application is a continuation of application Ser. No. 151,242, filed May 19, 1980 now abandoned.

TECHNICAL FIELD

This invention relates to an improvement in a process for refining crude, acidic tetrahydrofuran (THF).

BACKGROUND ART

THF is a commodity in the chemical industry, widely used as a solvent and as an intermediate in the preparation of various polymeric glycols useful in preparing polyurethanes.

One of the several methods used to commercially prepare THF is a three-step process which employs acetylene and formaldehyde as starting materials. In the first step of that process, acetylene and formaldehyde are reacted to form 1,4-butynediol, using a copper-acetylide complex as the catalyst. This reaction is described in U.S. Pat. Nos. 3,560,576 and 3,650,985, both to J. R. Kirchner.

In the second step, the butynediol formed in the first step is catalytically hydrogenated to 1,4-butanediol, using a Raney nickel catalyst. This procedure is described in British Pat. No. 1,242,358.

In the third step of that process, the butanediol from the second step is catalytically dehydrated and cyclized to THF using sulfuric acid as the catalyst, as described in U.S. Pat. No. 3,726,905 to J. S. Coates and V. J. Reilly.

The THF produced in that way is crude and must be refined if it is to meet commercial standards. This is commonly done by multi-step distillation.

Distillation is a generally satisfactory way of refining THF, except that the crude THF contains water and formic acid which attack and corrode the carbon steel of which distillation columns are ordinarily constructed. This corrosion can be controlled by eliminating the formic acid with base, and this is ordinarily done by simply adding large amounts of base to the crude THF. This excess of base, however, causes the formation of methacrolein, whose presence causes color formation in polymeric glycols made from the refined THF.

It is, of course, highly desirable to minimize this corrosion and to hinder the formation of methacrolein.

DESCRIPTION OF THE INVENTION

It has now been found, according to the invention, that the corrosion can be held within acceptable bounds and that the methacrolein content of the refined THF can be simultaneously kept within the industrially desirable limit of 30 ppm or less if the pH value of the crude THF is brought within the range 5–11, preferably 7–10, before it is fed to the distillation columns. Crude THF whose pH value is allowed to rise appreciably above about 11 shows a marked and unexpected rise in methacrolein content.

Crude THF from the third step reactor is ordinarily brought to a tank, where it is held briefly before it is fed to the distillation columns. The pH adjustment is made at this point, either by feeding an appropriate amount of an adjusting material into the THF stream entering the tank, or by adding the adjusting material directly to the tank. Normally, the motion imparted to the tank's contents by the entry and withdrawal of THF will uniformly distribute the adjusting material, but extraneous agitation or stirring can be employed if desired. The pH value of the THF is measured potentiometrically, with conventional electrodes placed either within the tank or in its outlet.

Sodium hydroxide or potassium hydroxide are ordinarily used as pH adjusting materials because of their availability and low cost. These are added to the THF in the form of an aqueous solution, preferably at a concentration of 20–25%, by weight.

The pH value of the THF can also be brought to within the desired range by adding a buffer such as a carbonate- or bicarbonate system, as is well-known. Use of such a system makes it possible to maintain the pH value of the crude THF within a specified range without using monitoring equipment.

The physical conditions in the holding tank require no change from the customary, as the process of the invention performs satisfactorily under all such conditions. Thus, temperatures can vary from the usual ambient to about 85° C., residence time of THF in the tank can vary from a few hours to several days, and the process can be run under nitrogen to hold down THF vapors and to prevent exposure of the THF to atmospheric oxygen.

After the pH adjustment has been made, the THF can be fed to the refining train, as before.

BEST MODE

Crude THF from a third step cyclization reactor is fed to a closed, vented holding tank at an average rate of about 185 liters per minute. Sodium hydroxide (25% by weight solution in water) at ambient temperature is fed into the entering THF stream at an average rate of about 19.5 kilograms of solution per hour, so that the average pH value of the THF is about 7.0.

After an average residence time in the tank of about 9.3 hours, the THF is fed into the first of four distillation columns for refining. Product THF from the last column has a methacrolein content of about 13 ppm.

We claim:

1. A process for refining crude acidic tetrahydrofuran made from acetylene and formaldehyde, the process comprising adding enough base to the crude tetrahydrofuran to bring its pH value to no more than about 11, but in sufficient amount to hinder the formation of methacrolein while inhibiting corrosion therein, and thereafter distilling the thus treated tetrahydrofuran.

2. The process of claim 1 in which the pH value of the crude tetrahydrofuran is brought to within the range 7–10.

3. The process of claim 1 or 2 in which the pH value is brought to the proper level with sodium hydroxide or potassium hydroxide.

4. The process of claim 1 or 2 in which the pH value is brought to the proper level with a buffer system.

* * * * *